US009486559B2

(12) United States Patent
Mazer et al.

(10) Patent No.: US 9,486,559 B2
(45) Date of Patent: Nov. 8, 2016

(54) METHODS OF TREATMENT WITH A BIORESORBABLE SCAFFOLD FOR NEUROLOGIC DRUG DELIVERY

(71) Applicant: Abbott Cardiovascular Systems Inc., Santa Clara, CA (US)

(72) Inventors: Terry B. Mazer, New Albany, OH (US); Stephen D. Pacetti, SanJose, CA (US); Brenna H. Lord, San Francisco, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 80 days.

(21) Appl. No.: 13/889,259

(22) Filed: May 7, 2013

(65) Prior Publication Data

US 2014/0336750 A1 Nov. 13, 2014

(51) Int. Cl.
*A61F 2/06* (2013.01)
*A61L 31/14* (2006.01)
*A61L 33/00* (2006.01)
*A61L 31/06* (2006.01)
*A61L 31/16* (2006.01)

(52) U.S. Cl.
CPC .............. *A61L 31/148* (2013.01); *A61L 31/06* (2013.01); *A61L 31/146* (2013.01); *A61L 31/16* (2013.01); *A61L 33/0011* (2013.01); *A61L 33/0047* (2013.01); *A61L 2300/254* (2013.01); *A61L 2300/256* (2013.01); *A61L 2300/416* (2013.01); *A61L 2300/45* (2013.01); *A61L 2300/604* (2013.01)

(58) Field of Classification Search
CPC . A61L 31/48; A61L 33/0047; A61L 33/0011
USPC .................... 623/1.43; 424/94.2, 94.6, 94.66
See application file for complete search history.

(56) References Cited

U.S. PATENT DOCUMENTS

| 7,135,038 | B1* | 11/2006 | Limon | 623/1.15 |
|---|---|---|---|---|
| 2008/0033522 | A1* | 2/2008 | Grewe et al. | 623/1.11 |
| 2011/0153005 | A1* | 6/2011 | Harder | 623/1.46 |
| 2013/0289082 | A1* | 10/2013 | Makriyannis | A61K 31/12 514/364 |
| 2014/0377319 | A1* | 12/2014 | Leuthardt | A61K 38/48 424/422 |

FOREIGN PATENT DOCUMENTS

| WO | WO 2012/145428 A2 | 10/2012 | | |
|---|---|---|---|---|
| WO | WO 2012145428 A2 * | 10/2012 | | A61K 38/48 |

OTHER PUBLICATIONS

Sellamuthu, Saravan et al. An Engineered Viral Protease Exhibiting Substrate Specificity for a Polyglutamine Stretch Prevents Polyglutamine-Induced Neuronal Cell Death. PLOS One. Jul. 2011. vol. 6. Issue 7. pp. 1-9.*
Sellamuthu (An Engineered Viral Protease Exhibiting Substrate Specificity for a Polyglutamine Stretch Prevents Polyglutamine-Induced Neuronal Cell Death, 2011—cited in the IDS filed on Apr. 29, 2014).*
Ge, Pengfei et al. Anti-protein aggregation is a potential target for preventing delayed neuronal death after transient ischemia. Medical Hypotheses. El Sevier. Medical Hypotheses 73 (2009) 994-995.*
Mayo Clinic. Diseases and Conditions Huntington's disease. Retrieved from the Mayo Clinic website on May 16, 2016: <http://www.mayoclinic.org/diseases-conditions/huntingtons-disease/basics/tests-diagnosis/con-20030685>.*
Parkinson's Disease Foundation. Understanding Parkinson's Disease. Retrieved from the Parkinson's Disease Foundation on May 16, 2016: <http://www.pdf.org/en/diagnosis>.*
Cramer et al., "ApoE-Directed Therapeutics Rapidly Clear β-Amyloid and Reverse Deficits in AD Mouse Models", Science 355, pp. 1503-1506 (2012).
Hemming et al., "Reducing Amyloid Plaque Burden via Ex Vivo Gene Delivery of an Aβ-Degrading Protease: A Novel Therapeutic Approach to Alzheimer Disease", PLoS Medicine vol. 4, issue 8, pp. 1405-1416 (2007).
Saltzman et al, "Amyloid pores from pathogenic mutations", Nature vol. 418, pp. 291-292 (2002).
Sarkar et al., "Rapamycin and mTOR-independent autophagy inducers ameliorate toxicity of polyglutamine-expanded huntingtin and related proteinopathies", Cell Death and Differentiation 16, pp. 44-56 (2009).
Selkoe "Clearing the Brain's Amyloid Cobwebs", Neuron vol. 32, pp. 177-180 (2001).
Sellamuthu et al., "An Engineered Viral Protease Exhibiting Substrate Specificity for a Polyglutamine Stretch Prevents Polyglutamine-Induced Neuronal Cell Death", PLoS One vol. 6, issue 7 (2011).
Sims et al., "Glutamic protease distribution is limited to filamentous fungi", FEMS Microbiology Letters 239, pp. 95-101 (2004).
Vartiainen et al., "Antimicrobial Activity of Glucose Oxidase-immobilized Plasma-activated Polypropylene Films", Packaging Tech. and Science 18, p. 243-251 (2005).
Oda, Kohei "New families of carboxyl peptidases: serine-carboxyl peptidases and glutamic peptidases," J. Biochem., Jul. 7, 2011, vol. 151, No. 1, pp. 13-25.
International Search Report and Written Opinion mailed on Jan. 5, 2016 in related PCT application No. PCT/US2014/036967, 24 pp.

\* cited by examiner

*Primary Examiner* — Scott Long
*Assistant Examiner* — Nghi Nguyen
(74) *Attorney, Agent, or Firm* — Squire Patton Boggs (US) LLP

(57) ABSTRACT

Bioresorbable scaffolds and methods of treatment with such scaffolds for neurologic disorders including Parkinson's disease, Huntington's disease, Alzheimer's disease, and brain neoplasms are disclosed. The bioresorbable scaffold includes a bioresorbable body and an active agent or drug associated with the body for treating or ameliorating the neurological disorder. The bioresorbable scaffold is implanted in the neurological vasculature brain or brain tissue to provide localized delivery of the drug or active agent. Embodiments of the invention include scaffolds that are partially bioresorbable or completely bioresorbable.

8 Claims, 2 Drawing Sheets

METHODS OF TREATMENT WITH A BIORESORBABLE SCAFFOLD FOR NEUROLOGIC DRUG DELIVERY

BACKGROUND OF THE INVENTION

Field of the Invention

This invention relates to bioresorbable implants and methods of using such implants for treatments of neurologic disorders.

Description of the State of the Art

This invention relates generally to treatment of neurologic disorders with endoprostheses that are adapted to be implanted in the central nervous system. An "endoprosthesis" corresponds to an artificial device that is placed inside the body.

Neurologic disorders include Huntington disease, Parkinsons's disease, Alzheimer's disease, and brain neoplasms such as tumors, gliomas and meningiomas. Such neurological diseases are typically not treated with endoprostheses, i.e., implantation of an endoprosthesis in the neurovasculature. Therapeutic treatment of many neurologic disorders has been primarily through systemic administration of active agents or surgery.

Patients with coronary artery disease are conventionally treated with percutaneous interventional procedures (angioplasty and stenting), coronary artery bypass grafting (surgery) and medications to improve blood flow to the heart muscle. In particular, stents are generally cylindrically shaped devices that function to hold open and sometimes expand a segment of a blood vessel or other anatomical lumen such as urinary tracts and bile ducts. A "lumen" refers to a cavity of a tubular organ such as a blood vessel. Stents are often used in the treatment of atherosclerotic stenosis in blood vessels, where "stenosis" refers to a narrowing or constriction of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

Stents are typically composed of a scaffold or scaffolding that includes a pattern or network of interconnecting structural elements or struts, formed from wires, tubes, or sheets of material rolled into a cylindrical shape. This scaffold gets its name because it physically holds open and, if desired, expands the wall of a passageway in a patient. Typically, stents are capable of being compressed or crimped onto a catheter to a reduced diameter so that they can be delivered to and deployed at a treatment site.

Delivery includes inserting the stent through small lumens using a catheter and advancing it to the treatment site. Deployment includes expanding the stent to a larger diameter once it is at the desired location. Mechanical intervention with stents has reduced the rate of restenosis as compared to balloon angioplasty.

Stents are also used as vehicles for providing biological therapy or drug delivery. Biological therapy uses medicated stents to locally administer a therapeutic substance. Effective concentrations at the treated site require systemic drug administration which often produces adverse or even toxic side effects. Local delivery is a preferred treatment method because it administers smaller doses of medication than systemic methods, but concentrates the drug at a specific site.

A medicated endoprosthesis may be fabricated by coating the surface of either a metallic stent or a polymeric scaffold with a polymeric carrier that includes an active or bioactive agent or drug. Polymeric scaffolding itself may also serve as a carrier of an active agent or drug.

In coronary applications in which the stent maintains patency of a vessel the stent must be capable of withstanding the structural loads, namely radial compressive forces, imposed on the stent as it supports the walls of a vessel. Therefore, a stent must possess adequate radial strength. Radial strength, which is the ability of a stent to resist radial compressive forces, relates to a stent's radial yield strength and radial stiffness around a circumferential direction of the stent. A stent's "radial yield strength" or "radial strength" (for purposes of this application) may be understood as the compressive loading, which if exceeded, creates a yield stress condition resulting in the stent diameter not returning to its unloaded diameter, i.e., there is irrecoverable deformation of the stent. When the radial yield strength is exceeded the stent is expected to yield more severely and only a minimal force is required to cause major deformation. Radial strength is measured either by applying a compressive load to a stent between flat plates or by applying an inwardly-directed radial load to the stent.

Some treatments with stents require its presence for only a limited period of time. Once treatment is complete, which may include structural tissue support and/or drug delivery, it may be desirable for the stent to be removed or disappear from the treatment location. One way of having a stent disappear may be by fabricating a stent in whole or in part from a material that erodes, resorbs or disintegrates through exposure to conditions within the body. Stents fabricated from biodegradable, bioabsorbable, bioresorbable, and/or bioerodible materials such as bioabsorbable polymers can be designed to completely resorb only after the clinical need for them has ended.

SUMMARY OF THE INVENTION

Embodiments of the present invention include an implantable bioresorbable scaffold for delivering a drug for treating a neurological disease in the central nerve system, comprising: a bioresorbable body; and an active agent associated with the bioresorbable body, wherein when the scaffold is implanted in a patient, the active agent, upon coming into contact with a protein that causes the neurological disease, the active agent renders the protein nonpathogenic.

Embodiments of the present invention include a method for treating or ameliorating a neurological disease in the central nervous system, comprising: implanting a bioresorbable scaffold in a blood vessel of the central nervous system of a patient in need of treatment or amelioration a neurological disease, wherein the bioresorbable scaffold comprises an active agent; and allowing the active agent from the implanted scaffold to come into contact with a protein that causes the neurological disease and to render the protein nonpathogenic.

Embodiment of the present invention include an implantable bioresorbable scaffold for delivering an active agent for treating Alzheimer's disease in the central nerve system, comprising: a bioresorbable body; an active agent associated with the bioresorbable body, wherein when the scaffold is implanted in a patient, the active agent promotes clearance or removal of the amyloid plaque found in brain tissue of patients with Alzheimer's.

Embodiments of the present invention include a method for treating or ameliorating Alzheimer's disease, comprising: implanting a bioresorbable scaffold in a blood vessel of the central nervous system of a patient in need of the treatment or amelioration of Alzheimer's disease, wherein the bioresorbable scaffold comprises an active agent; and allowing the active agent from the implanted scaffold to come into contact with brain tissue affected with amyloid plaque and to promote clearance or removal of the amyloid plaque.

Embodiments of the present invention include an implantable bioresorbable scaffold for delivering an active agent for treating a brain neoplasm, comprising: a bioresorbable body, an antineoplastic agent associated with the bioresorbable body, wherein when the scaffold is implanted in a patient, the antineoplastic agent contacts brain tissue affected with the neoplasm and kills or slows growth of malignant cells in the tissue.

Embodiments of the present invention include a method for treating or ameliorating a brain neoplasm, comprising: implanting a bioresorbable scaffold in a cerebral artery supplying blood to a brain neoplasm of a patient in need of the treatment or amelioration thereof, wherein the bioresorbable scaffold comprises an antineoplastic drug; and allowing the drug from the implanted scaffold to come into contact with brain tissue affected with the neoplasm and kills or slows growth of malignant cells in the tissue.

DETAILED DESCRIPTION OF THE INVENTION

All patents, patent publications, and other publications referred to in this application are incorporated by reference herein.

Embodiments of the present invention include a bioresorbable implant or device, such as a scaffold, and methods of treatment with such implants for neurologic disorders including Parkinson's disease, Huntington's disease, Alzheimer's disease, and brain neoplasms. The bioresorbable implant includes a bioresorbable body, such as a scaffold structure and an active agent or drug associated with the body for treating or ameliorating the neurological disorder. The bioresorbable implant is implanted in the neurological vasculature of the brain or brain tissue to provide localized delivery of the drug or active agent. Embodiments of the invention include implants that are partially bioresorbable or completely bioresorbable. The bioresorbable body may completely resorb upon completion of active agent delivery. The complete or partial resorption of the device allows implantation of another device, the same or different, at or overlapping the implant site of the resorbed device.

The use of a bioresorbable implant for drug delivery to the brain has several advantages.

First, a tubular implant such as a scaffold once implanted is well apposed to the vessel wall and will become embedded in the vessel wall and reendothelialized. The problems with the impermeability of the blood-brain barrier are well known. The blood brain barrier only allows small molecules to enter the brain. The blood vessels and capillaries of the central nervous system have endothelium with tight junctions which do not exist in vasculature outside of the central nervous system. A scaffold implanted in the arterial system of the brain will bypass the blood-brain barrier.

Second, the maximum payload of drug that can be delivered is higher for a bioresorbable implant than for non-bioresorbable implant. As much as the entire scaffold in terms of the bulk of the scaffold can be used as a reservoir for drug delivery. Resorption of the scaffold will result in release of the entire drug payload.

Third, after the drug therapy is completed, the implant will resorb, removing any biocompatibility issues arising from a permanent presence.

Fourth, targeted or local delivery of the drug from the implant to the brain tissue will reduce systemic exposure to the drug. Thus, higher doses of drugs or more toxic drugs may thus be used. Additionally or alternatively, a reduction in systemic side effects may be realized. Lastly, active agents with short in vivo lifetimes can be released and still achieve efficacious concentrations in the target tissue.

Fifth, if additional drug therapy is required, another implant may be implanted at or near the same implant site.

Figure 1:
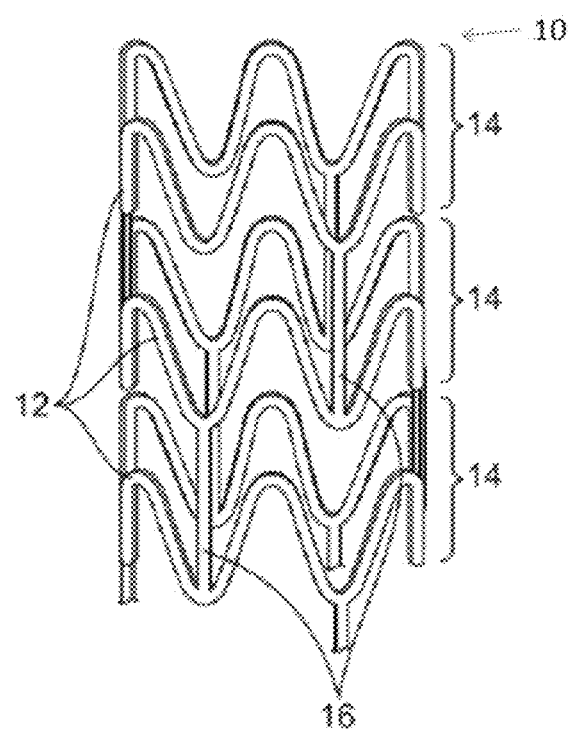
FIG. 1 depicts an exemplary scaffold.

Various embodiments of the structure of an implant may be used. The implant may have a tubular structure with walls surrounding an inner lumen. An exemplary tubular implant is a stent or scaffold structure. A scaffold may include a pattern or network of interconnecting structural elements or struts. An exemplary structure of a scaffold is shown in FIG. 1. FIG. 1 depicts a scaffold 10 which is made up of struts 12 with gaps between the struts. Scaffold 10 has interconnected cylindrical rings 14 connected by linking struts or links 16. The outer surface of the struts that faces the tissue is the abluminal surface and the inner surface of the struts facing the lumen of the vessel is the luminal surface. Scaffold 10 may be formed from a tube (not shown). The structural pattern of the device can be of virtually any design. The embodiments disclosed herein are not limited to scaffolds or to the scaffold pattern illustrated in FIG. 1. Such a tube can be formed, for example, by extrusion, dip coating onto a form such as a mandrel, or injection molding.

A scaffold such as scaffold 10 may be fabricated from a polymeric tube or a sheet by rolling and bonding the sheet to form the tube. The tube may initially have no holes or gaps. The scaffold pattern can then be formed with laser cutting.

The embodiments are easily applicable to other patterns and other devices. The variations in the structure of patterns are virtually unlimited. Other tubular implant structures include helical structures or tubular structured formed by braiding filaments.

In general, the walls of the implant structure can have gaps, holes, fenestrations that extend between the inner and outer surface of a wall so that the tissue of the walls of the vessel is exposed to the lumen through the gaps or holes. The ratio of the area of the abluminal surface of the struts to the total vessel surface area (scaffold abluminal surface and area of gaps) may be 5% to 50%. This is also known as the scaffold/artery ratio.

A scaffold well-apposed to the vessel wall, with the scaffold/artery ratio described above facilitates reendothelialization of the scaffold. To achieve good reendothelialization, the scaffold should not induce chronic inflammatory response. Such a response may also jeopardize any protease, protein or antibody therapy as the attracted monocytes, macrophages, lymphocytes, eosinophils and neutrophils could degrade the active agent.

The diameter of the tubular implants as-fabricated (e.g., as laser cut) or as-deployed may be 2 to 5 mm, or more narrowly, 2 to 2.2 mm, 2.2 to 2.5 mm, 2.5 to 3 mm, 3 to 3.5 mm, 3.5 to 4 mm or 4 to 5 mm. The wall thickness of the implants may be 25 to 200 microns, or more narrowly, 25 to 50 microns, 50 to 100 microns, 100 to 150 microns, or 150 to 200 microns.

In other embodiments, a tubular implant can have porous walls that include a three dimensional network of interconnected pores. Any of the disclosed structures can have porous walls. The porous structure can be open or closed cell. The pore size (e.g., diameter) of any pores or the average pore size may be 10 to 100 microns, 1-10 microns, 10-100 microns or greater than 100 microns. A porous polymer tube may be formed, for example, by extrusion with supercritical carbon dioxide.

Typically, stents are capable of being compressed or crimped onto a catheter to a reduced diameter so that they can be delivered to and deployed at a treatment site. Delivery includes inserting the stent through small lumens using a catheter and advancing it to the treatment site. Delivery of a stent or scaffold into the neurovasculature of the brain can include percutaneous access through the femoral artery or radial artery.

Deployment includes expanding the stent to a larger diameter once it is at the desired location. The delivery diameter of the tubular implants may be 1.5 to 2.5 mm.

The tubular implant may be balloon expandable or self-expandable. In the case of a balloon expandable device, the geometry of the device can be an open cell structure similar to the stent patterns disclosed herein or a closed cell structure. In a balloon expandable device, when the device is crimped from a fabricated diameter to a crimped or delivery diameter onto a balloon, structural elements plastically deform. Aside from incidental recoil outward, the device retains a crimped diameter without an inward force on the crimped device due to the plastically deformed structural elements. When the device is expanded by the balloon, the structural elements plastically deform again.

In the case of a self-expandable device, when the device is crimped from a fabricated diameter to a crimped or delivery diameter on a balloon, structural elements deform elastically. Therefore, to retain the device at the crimped diameter, the device is restrained in some manner with an inward force, for example with a sheath or a band. The crimped device is expanded to an intended expansion or deployment diameter by removing the inward restraining force which allows the device to self-expand to the intended deployment diameter. The structural elements deform elastically as the device self-expands.

An as-fabricated diameter of an implant may be 0.7 to 1 times an intended deployment diameter or any value in between and including the endpoints. An as fabricated diameter may also be 1 to 1.5 times the intended deployment diameter, or any value in between and including the endpoints.

An implant such as a scaffold may be made partially or completely out of a bioresorbable material or materials. After the implant has served its function of drug delivery, the implant may partially or completely disappear from the treatment location by resorbing. Embodiments can include implants fabricated from biodegradable, bioabsorbable, bioresorbable, and/or bioerodible materials such as bioresorbable polymers or bioerodible metals that can be designed to completely erode only after the clinical need for them has ended. The device may be configured to completely erode away within 3 months, 3 to 6 months, 6 to 12 months, 12 to 18 months, 18 months to 2 years, or greater than 2 years.

Bioresorbable polymers for fabricating implants such as scaffolds include relatively high strength and high modulus polymers including, but not limited to, poly(L-lactide) (PLLA), poly(L-lactide-co-D,L-lactide) (PLDLA) and polyglycolide (PGA) and copolymers and blends thereof, for example, poly(L-lactide-co-glycolide) (PLGA). The PLGA can have a mole % of GA between 5 and 50 mol %, or more narrowly, 5-15 mol %. The PLGA can have a mole % of (LA:GA) of 85:15 (or a range of 82:18 to 88:12), 50:50 (or a range of 48:52 to 52:48), 95:5 (or a range of 93:7 to 97:3), or commercially available PLGA products identified being 85:15, 50:50, or 95:5 PLGA. High modulus polymers may have a Tg greater than body temperature or 37 deg C, or greater than 10 or greater than 20 deg C above human body temperature or 37 deg C.

Bioresorbable polymers for fabricating implants such as scaffolds include relatively low modulus polymers including, but not limited to, poly(4-hydroxybutyrate) (P4HB), polycaprolactone (PCL), poly(trimethylene carbonate) (PTMC), poly(butylene succinate) (PBS), and poly(p-dioxanone) (PDO). The implant material can include blends of low modulus polymers with high modulus polymers or other low modulus polymers, copolymers (block, random, or alternating) of low modulus polymers with high modulus polymers or other low modulus polymers, or any combination thereof. Such low modulus polymers may have a Tg less than body temperature or 37 deg C, less than 25 deg C, or less than 0 deg C.

In some embodiments, the radial strength of the scaffold can be relatively low since the primary purpose of the device is drug delivery and not to maintain patency of a vessel an increased diameter. The radial strength of the scaffold immediately after expansion to an intended deployment diameter in a vessel may at most be the radial pressure required for the device to maintain contact with the vessel wall to remain lodged in the vessel. The radial strength in this case may be less than 150 mm Hg, 100 to 150 mm Hg, 150-200 mm Hg, 1 to 10 mm Hg, or less than 100 mm Hg. The radial strength can be based on a diameter of an as-fabricated device prior to crimping and expansion or a device after it has been crimped and expanded to an intended deployment diameter. In this case, the implant material may have a modulus of elasticity less than 1.5 GPa, 1 GPa, or 0.5 GPa or 0.5 to 1 GPa at 25 deg C, 37 deg C, or in a range of 25 to 37 deg C.

In other embodiments, the radial strength of the scaffold can be high enough to maintain patency of a vessel at an increased diameter once implanted. In such embodiments, the radial strength can be greater than 200 mm Hg, 200-300 mm Hg, or higher than 350 mm Hg. In this case, the implant material may have a modulus of elasticity greater than 2 GPa, 3 GPa, 5 GPa, 7 GPa, or 9 GPa.

The drug delivery implant may include a base substrate or structure such as a scaffold, as described herein. The active agents may be incorporated or associated with the implant substrate in various ways.

An active agent or agents may be distributed within a part or throughout the implant substrate within the material of the implant.

An active agent coating may be disposed over an entire surface of the implant substrate or over a portion of the surface of the implant substrate. A coating with a particular agent or agents may be disposed exclusively over an inside surface, outside surface, or both. A drug delivery coating thickness may be 1 micron, 2 to 3 microns 3 to 4 microns, 4 to 6 microns, 6 to 10 microns, 10 to 20 microns, or greater than 20 microns. Application of a coating can be through dip-coating, spray-coating, ink-jet printing, direct dispense, or roller-coating.

At least a portion of the implant may be porous and the active agent may be distributed through the porous network. An entire scaffold body may be porous, the coating may be porous, or both.

An implant may be a tube or formed from a tube (e.g., in the case of a scaffold) having two layers, an inside layer and outside layer. The layers can be made of different polymers and be different thickness. The two layer scaffold can be formed by coextruding layers of two types of polymers to form a two layer tube and forming a scaffold from the tube by laser cutting the two layer tube. One or both of the layers can be porous. One or both of the layers may include an active agent.

Active agent incorporated within a polymer can be mixed, dispersed, or dissolved within the polymer.

The active agents can be incorporated into a carrier polymer which can include, but is not limited to, polylactide-based polymers such as poly(D,L-lactide) and copolymers thereof, polyglycolide-based polymers such as polyglycolide and copolymers thereof. Carrier polymers can also include other polyesters such as polycaprolactone, polyanhydrides such as poly(sebacic anhydride), polyhydroxyalkanoates such as poly(3-hydroxybutyrate), polyester-amide, hydrophilic polymers such as polyethylene glycol/oxide, and polyvinylpyrrolidone. Carrier polymers also include blends of the disclosed polymers and copolymers of the disclosed polymers. Additional carrier polymers include hydrogels made from polyethylene glycol, polyvinypyrolidone, polysaccharide, dextran, hyaluronic acid, glycosaminoglycans, sugar, or copolymers thereof with a biodegradable polymer such as PDLLA, PGA, or another family of the carrier polymer.

Huntington's disease is a neurodegenerative genetic disorder that leads to production of a protein defect or pathogenic protein. A genetic basis for Parkinsons's and Alzheimer's diseases is not firmly established. These diseases are conjectured to be due to some combination of genetics, injury, environmental factors and other causes. However, as with Huntingtons's, hallmarks of Parkinson's and Alzheimer's are defective and pathogenic proteins which appear to act as prions. For Parkinson's and Huntington's diseases, the protein defect is a polyglutamine that is above a certain length. Specifically, polyglutamine that is 36 or more glutamine units in length is pathogenic. A polyglutamine that has 35 or less repeat units of glutamine is nonpathogenic. The pathogenic proteins for Huntington's, Parkinson's, and Alzheimer's diseases originate in the same point in the brain. The brain naturally attempts to control these proteins by producing proteases, such as capsases, that attack these polyglutamines. However, in the brain, proteases are located in proteosomes which are not highly effective at clearing these disease produced 36 or more mer polyglutamines. In the process, the polyglutamines are only partially broken down and are actually converted into prions that spread the disease throughout the brain. A prion is an infectious protein particle in a misfolded form lacking nucleic acid; thought to be the agent responsible for scrapie and other degenerative diseases of the nervous system. When a prion enters a healthy organism, it induces existing, properly folded proteins to convert into the disease-associated, prion form. The prion acts as a template to guide the misfolding of more proteins into prion form. These newly formed prions can then go on to convert more proteins themselves; this triggers a chain reaction that produces large amounts of the prion form Embodiments of the invention include a bioresorbable device including a bioresorbable body and an active agent associated with the bioresorbable body for treating a neurologic disease caused by the pathogenic protein. The bioresorbable body may have the structure of a scaffold. The active agent, upon coming into contact with a protein that causes the neurological disease, renders the protein nonpathogenic. A method of treatment includes implanting the bioresorbable device in a blood vessel of the central nervous system of a patient in need of treatment or amelioration of a neurological disease and allowing the active agent from the implanted device to come into contact with a protein that causes the neurological disease and renders the protein nonpathogenic.

The active agent controls or prevents accumulation of the protein defect which controls progression of the disorder and symptoms associated with the disorder. Treatment with the implant thus may halt or slow progression of the disorder which delays appearance or worsening of the symptoms and prolongs the lifetime of the patient.

The drug or active agent can include a protease. In general, a protease is any enzyme that conducts proteolysis on a protein. Proteolysis is the breakdown of proteins into smaller polypeptides or amino acids. The breakdown generally occurs by the hydrolysis of the peptide bonds that link amino acids together in the polypeptide chain forming the protein.

The proteases can either break specific peptide bonds (limited proteolysis), depending on the amino acid sequence of a protein, or break down a complete peptide to amino acids (unlimited proteolysis). The proteases may also cross-link a pathogenic protein, making the protein nonpathogenic or inactive.

A protease associated with the scaffold for treating Huntington's and Parkinson's disease renders polyglutamine nonpathogenic. The protease can cleave glutamine-glutamine bonds upon contact with the polyglutamine. Proteolysis by the protease controls the accumulation of polyglutamine. The protease may intervene in the initial events leading to pathogenesis in these diseases or limit further progression of the diseases. Doses of protease administrable by, for example, a 12 mm long scaffold range from as low as 50 µg for protease located in a coating to as high as 5 mg for protease incorporated into the scaffold backbone.

The protease associated with the device prior to implantation may be in a pro-form or inactive state to prevent the protease from cleaving itself. The protease in the pro-form is unable to cleave proteins or other protease. Upon implantation the protease may be activated or changed to an active form so that it can cleave pathogenic proteins. The protease may be activated by a stimulus naturally occurring in the physiological environment of the patient. For example, the protease may be activated by a protein in bodily fluids. Alternatively, the protease may be activated by a local change in conditions arising from the device. For example, a local decrease in pH triggered by the acidic degradation products of the bioresorbable material of the device may trigger activation.

The protease may be an engineered protease exhibiting substrate specificity for a polyglutamine stretch or sequence of amino acids in the polyglutamine. The sequence may correspond to 3 or more amino acids. A study has shown that proteolytic cleavage of polyglutamine stretches by an exemplary protease could be an effective modality for the treatment of polyglutamine diseases. Sellamuthu S, et al. (2011) An Engineered Viral Protease Exhibiting Substrate Specificity for a Polyglutamine Stretch Prevents Polyglutamine- Induced Neuronal Cell Death. PLoS ONE 6(7): e22554. doi:10.1371/journal.pone. 0022554. In this study, Hepatitis A virus (HAV) 3C protease (3CP) was subjected to engineering using a yeast-based method known as the Genetic Assay for Site-specific Proteolysis (GASP). Analysis of the substrate specificity revealed that 3CP can cleave substrates containing glutamine at positions P5, P4, P3, P1, P2', or P3', but not substrates containing glutamine at the P2 or P1' positions. To accommodate glutamine at P2 and P1', key residues comprising the active sites of the S2 or S1' pockets were separately randomized and screened.

Glutamic proteases are also found in filamentous fungi. These include the A4 family of aspatic endopeptidases and the Eqolisins. (Sims A H, Dunn-Coleman N S, et al. Glutamic Protease distribution is limited to filamenous fungi. FEMS Microbio Lett 2004; 239: 95-101.) Fungal species producing glutamic proteases include *Phanerochaete chrysosporium, Aspergillus fumigatus, Aspergillus nidulans, Aspergillus niger, Magnaporthe grisea, Neurospora crassa, Fusarium graminearum*, and *Trichoderma reesei.*

The proteases digest the long protein chains into short fragments, splitting the peptide bonds that link amino acid residues. The proteases can include those that cleave or detach peptide bonds only in selected portions of a pathogenic protein such as polyglutamine. Exoproteases or exopeptidases detach the terminal amino acids from the protein chain. Endoproteases or endopeptidases cleave only internal peptide bonds of a protein.

The proteases can include transproteases or transpeptidases which is an enzyme that catalyzes a transpeptidation reaction which is the transfer of an amino or peptide group from one molecule to another. In the course of a proteolysis, the transprotease forms an acylated enzyme as an intermediate in the process.

The protease(s) associated with the device can include one or any combination of an exoprotease; an endoprotease; or transglutaminase. In particular, a protease associated with the scaffold may be capable of cleaving terminal or internal glutamine-glutamine bonds of the polyglutamine.

The active agent such as the protease that renders the pathogenic protein nonpathogenic may be associated with the scaffold in various ways, as described herein. The active agent may be distributed throughout the bioresorbable body, within a coating including a carrier polymer on at least a portion of the surface of the device, within at least one of an abluminal or luminal layer of a scaffold, or on the surface of the device without a carrier polymer, or any combination of thereof.

It is the actions of caspaces and calpains which attempt to cleave polyglutamine sequences thus creating pathogenic proteins. An alternative approach is the release of molecules that will inhibit the action of caspaces and calpains. Such inhibitors can be small molecules, antibodies, peptides, or proteins.

Alzheimer's and Parkinson's diseases are associated with the formation in the brain of amyloid fibrils from β-amyloid and α-synuclein proteins. (Lashuel H A, Hartley D, et al. Amyloid pores from pathogenic mutations. Nature 2002; 418:291.) For local delivery, there are several strategies involving proteases for the treatment of Alzheimers disease. The enzyme β-secretase has been implicated in cleaving the amyloid precursor protein (βAPP). Consequently, release of an inhibitor to β-secretase is one strategy to inhibit formation of the β-amyloid plaque found in Alzheimer's. Proteases capable of degrading β-amyloid include insulysin, neprilysin, plasmin, uPA/tPA, endothelin converting enzyme-1, and matrix metalloproteinase-9 (Selkoe D J. Clearing the Brain's Amyloid Cobwebs. Neuron 2001; 32:177-180.).

In some embodiments, the active agent may be releasable from the scaffold. Upon implantation, the active agent may be released from the device to the blood stream or tissue. Active agent on the surface may be released directly from the surface. Active agent distributed within a coating carrier polymer or with the polymer of the scaffold may be released by diffusion through polymer(s) and from the surface of the device. In such embodiments, the active agent is not bound in such a way that diffusion of the active agent is prevented. The release through diffusion of a polymer provides controlled release of the active agents. The active agents may be released over a period of 1 day to 2 weeks, 2 weeks to 6 months, 2 weeks to 1 month, 1 to 2 months, 2 to 5 months, 2 to 6 months, or greater than 6 months.

In other embodiments, the active agent is immobilized on or within the device such that release of the active agent through diffusion or directly from a surface of the implant is prevented. The active agents remain on or in scaffold for a period of time until resorption of device material allows release of the active agent. Therefore, the release of the immobilized active agents is controlled by the resorption rate of scaffold material.

"Immobilized" generally refers to the inability of an agent molecule to diffuse away from a location in or on a substrate material, such as a coating or scaffold material. In the context of an immobilized agent in or on a bioabsorbable polymer, the agent is incapable of diffusing away from its location in or on the coating material without the chemical breakdown of the biodegradable substrate material that is directly or indirectly preventing the agent from diffusing. Indirect or direct bonding of the immobilized agent to the substrate prevents the agent from diffusing. Thus, the immobilized agent can diffuse away from a substrate such as a coating polymer if the coating material that directly or indirectly binds it to the coating absorbs away.

Specifically, for both bulk and surface eroding polymers, exposure of a carrier polymer of a coating or scaffold polymer to bodily fluids causes hydrolytic degradation of the polymer which results in chain scission of the coating polymer. As degradation proceeds, the molecular weight of the species is reduced to a level that the degradation products are soluble in the bodily fluids and diffuse away to be metabolized or excreted.

The active agents may be immobilized, for example, by covalent bonds to the bioresorbable polymer of a scaffold or carrier polymer of a coating. For example, the proteases may be immobilized by a covalent bond (such as an amide bond) to an ester grafted to a polymer of the scaffold or coating.

In further embodiments, the scaffold can include both releasable and immobilized active agents.

In further embodiments, the active agent may be associated with a plurality of releasable particles incorporated within or on a bioresorbable body or scaffold. After implantation, the particles can be released from the scaffold. After release, the particles can be transported downstream from the implant site of the device. The active agent may be incorporated in or on the particles. The active agent can be encapsulated by particle material, dispersed within particle material, at a surface of the particle, or any combination thereof.

The particles may be incorporated in or on a bioresorbable body such as a scaffold in various ways. The particles can be disposed within depots or holes at the surface of the scaffold, disposed in a coating on the surface of the scaffold, or embedded or dispersed throughout the scaffold. In one embodiment, the release of the particles may be due in whole or in part to erosion or resorption of coating material, substrate material, or material which binds the particle to or within the scaffold.

In some embodiments, the active agent can be releasable from the particles directly from a surface or through diffusion from the particle material. The active agent can be released from the particles prior to and after release of the particles from the scaffold. The active agents can be immobilized in or on the surface of the particles. Immobilized active agent may eventually be released from the particle due to resorption of particle material.

When the particles are released, the active agent associated with the particles may contact pathogenic proteins downstream from the implant and render them nonpathogenic. The released active agent may also inhibit endogenous enzymes that lead to the formation of pathogenic proteins. The particles may be designed to have or selected to have an affinity to a portion of downstream vasculature. Such particles may selectively bind to a portion, e.g., by incorporating a peptide or an antibody fragment with affinity to receptors found on endothelial cells of the microvasculature into the surface of the particles. The bound particles may then provide sustained neutralizing of pathogenic proteins by releasable active agents, immobilized active agents, or both.

The particles may have a characteristic length (e.g., diameter) in the range of 10 to 100 nm, 100 to 500 nm, 500 nm to 1 micron, 1 micron to 10 microns. Methods for the manufacture of particles are well known to those skilled in the art.

The particle material can be a biostable polymer, biodegradable polymer, bioabsorbable polymer, bioresorbable polymer, metallic, or ceramic. Such particles may be coated with an active agent. Exemplary bioresorbable polymers include the polyesters disclosed herein. Additional bioresorbable polymers include surface eroding polymers including polyanhydrides and polyorthoesters. The particles can also encapsulate one or more active agents by having an outer shell of polymer, metal, or ceramic with an inner compartment containing one or more active agents. Encapsulating the agents with a surface eroding polymer can delay the release of the active agents for a period of time. Alternatively, the particle may be formed from a precipitate of neat drug.

The active agent may be in an encapsulated state in nanoparticles, nanocapsules, microparticles, microcapsules, liposomes, micelles, polyplexes, and polymerosomes.

To maximize surface area, and interaction of the active agent with tissue, at least a portion of the scaffold may be porous with protease immobilized throughout the porous network. The pathogenic protein diffuses into the pores which is then cleaved into smaller fragments which diffuse out of the scaffold. The porous network provides a larger surface area for deactivation of the pathogenic protein.

In other embodiments, the device may be made from hydrophilic copolymers can have components that are bioresorbable, water soluble, gel forming, or any combination thereof. Such polymers may include polyethylene oxide (PEO) or polyethylene glycol (PEG), and polyvinylpyrrolidone (PVP), polyvinyl alcohol (PVA), hyaluronic acid, dextran, glycosaminoglycans, and gelatin. The device may be made from copolymers of such hydrophilic polymers and the bioresorbable polymers disclosed herein. The bioabsorbable body, the coating, or both may be made from such polymers. Upon implantation, the hydrophilic polymer containing portion of the polymer may contain up to 50 wt % of water. The device made from such polymer may be porous to allow water to facilitate permeation into the hydrophilic polymer.

Additionally, a woven scaffold composed of fibers or braided fibers maximizes the surface area for immobilization of proteases or proteolytic enzymes. A covered scaffold design is another embodiment with large surface area. The cover may be a film covering some or all of the gaps in the wall of the scaffold. The film may be made of a bioresorbable polymer, such as any of those disclosed herein. The cover may include releasable or immobilized active agent on the surface or distributed within and throughout the cover. The cover may also be porous, as described herein. The active agent in the pores may be releasable or immobilized in the pores.

Parkinson's and Huntington's disease initiates in the same region of the brain called the substantia nigra, which is part of the basal ganglia. The blood supply to the basal ganglia comes primarily from the middle cerebral artery, in particular, the lenticulostriate branches. These are small branches from the middle cerebral artery that penetrate the basal ganglia.

The bioresorbable device may be implanted in the middle cerebral artery, in particular, the lenticulostriate branches. In some embodiments, the device may be implanted upstream of the substantia nigra region or the basal ganglia. In such embodiments, the proteases may be releasable as described herein so that the released proteases move downstream to the region to deactivate the pathogenic proteins. Released substances to inhibit select endogenous enzymes responsible for plaque formation can be delivered similarly. The device implanted upstream may further release particles including proteases. The particles may be designed to bind to vasculature at the region or lenticulostriate branches. The particles may release proteases or include immobilized proteases that remain with the bound particles to continuously deactivate pathogenic proteins.

A device including immobilized proteases may be implanted downstream of the substantia nigra region or the basal ganglia. In this location, the scaffold allows for the continuous removal of the pathogenic proteins with proteolytic hydrolysis into small pieces that are not prions and that proteosomes could then remove without getting inactivated or clogged. The device may provide protease(s) that allow for optimum efficiency and continuous cleaning of the enzyme surface for maximum life.

In further embodiments, an active agent for treating or ameliorating Huntington's or Parkinson's disease includes an antibody to polyglutamine. The antibody may include epitope or antigenic determinant to flag the polyglutamine for removal by leucocytes, inflammatory cells, or phagocytic cells.

With Huntington's disease, the polyglutamines behave like prions so the disease should be treated before symptoms occur to keep the disease from spreading throughout the brain. The bioresorbable scaffold may be implanted in the brain of a patient prior to disease symptoms, for example, prior to prion production. In this way, the time before disease symptoms appear could be lengthened. The device may be implanted early in the life of the patient, for example, in the second or third decade of life. In addition to prolonging life, such treatment may significantly reduce the cost of treatment and timeline.

Alzheimer's patients develop an amyloid plaque that is protein based which is different from the pathogenic protein of Huntington's and Parkinson's. Novel active agents that are being investigated for Alzheimer's are antibodies that promote clearance or removal of the amyloid plaque found in brain tissue of patients with Alzheimer's. These are currently being administered systemically in clinical trials. The specific compounds are Bapineuzumab from Johnson & Johnson, Solanezumab from Eli Lily, and Gammagard from Baxter international Inc. Local delivery would be a more efficient use of the drug.

Bexarotene (Targretin) produced a dramatic improvement in mice with Alzheimer's disease (AD) symptoms. Cramer, P E, et al. Published Online Feb. 9 2012 Science 23 Mar. 2012: Vol. 335 no. 6075 pp. 1503-1506 DOI: 10.1126/science. 1217697. Bexarotene, which is an oral retinoid that has been FDA-approved for cancer since 2000, may activate retinoid X receptors on brain cells. This activation could increase concentrations of apolipoprotein E, a fat-protein complex that removes excess amyloid in the fluid-filled space between neurons. Bexarotene may also convert microglia into their alternative activation state, allowing amyloid beta (Aβ) phagocytosis.

When used in mice, the drug was successful in removing the buildup of amyloid plaque in the brain as well as reversing cognitive symptoms and memory deficits. Bexarotene is usually administered orally for cutaneous lymphoma.

Further embodiments include a bioresorbable device for treating or ameliorating Alzheimers including a bioresorbable body including an active agent that when contacted with brain tissue affected with amyloid plaque, promotes clearance or removal of the amyloid plaque. A method for treating or ameliorating Alzheimer's disease includes implanting the bioresorbable scaffold in a blood vessel of the central nervous system of a patient in need of the treatment or amelioration of Alzheimer's disease. The drug is allowed to contact brain tissue affected with amyloid plaque and to promote clearance or removal of the amyloid plaque. The active agent may include Bexarotene, Bapineuzumab, Solanezumab, or Gammagard. The various embodiments disclosed for associating active agents with a bioresorbable device apply the above-mentioned active agents for the treatment of Alzheimer's disease.

Further embodiments of a bioresorbable device for treating or ameliorating Alzheimer's include a bioresorbable body and a protease associated with the body that catabolizes amyloid-β protein. Doses of protease administrable by, for example, a 12 mm long scaffold range from as low as 50 ug for protease located in a coating to as high as 5 mg for protease incorporated into the scaffold backbone. The protease, upon coming into contact with a protein that causes the neurological disease, renders the protein nonpathogenic. A method of treatment includes implanting the bioresorbable device in a blood vessel of the central nervous system of a patient in need of treatment or amelioration of Alzheimer's disease and allowing the protease to come into contact with amyloid-β protein and rendering the protein nonpathogenic through catabolism. An exemplary protease is neprilysin. Ex vivo gene delivery of neprilysin has been shown to reduce amyloid plaque burden in transgenic mice expressing human β-amyloid precursor protein (APP). Hemming M L, Patterson M, Reske-Nielsen C, Lin L, Isacson O, et al. (2007) PLoS Med 4(8): e262. doi:10.1371/journal.pmed.0040262. The various embodiments disclosed for associating active agents, particularly proteases, with a bioresorbable device apply to proteases that catabolize amyloid-β protein for the treatment of Alzheimer's disease.

In further embodiments, an active agent for treating or ameliorating Alzheimer's disease includes an antibody to amyloid plaque. The antibody may include epitope or antigenic determinant to flag the amyloid plaque for removal by leucocytes.

There are further adjunctive pharmacological therapies that may be used in addition to delivery of proteases, enzyme inhibitors, antibodies or small molecules. Rapamycin and other mTOR inhibitors mitigate the toxicity of polyglutamine via upregulation of an autophagy pathway (Sarkar S, Ravikumar B, et al. Rapamycin and mTOR-independent autophagy inducers ameliorate toxicity of polyglutamine expanded huntingtin and related proteinopathies. Cell Death and Diff 2009; 16:46-56). Other mTOR inhibiting compounds that could be used in this role are everolimus, zotarolimus, temsirolimus, deforolimus, ridaforolimus, merilimus, biolimus, umirolimus, myolimus, and novolimus. These compounds also are antiproliferative agents and reduce neointimal proliferation with the effect of improving patency of the scaffolded vascular segment. Intravascular stents and scaffolds may also experience a very low rate of thrombotic occlusion. When this risk is present, it is treated by systemic dual antiplatelet therapy consisting of aspirin combined with an antiplatelet drug such as ticlopidine, clopidogrel, prasulgrel, or ticagreleor. While these may be indicated for a short duration after implantation of the neurological drug delivery scaffold, the scaffold itself can also release antithrombotic agents including heparin, hirudin, and IIbIIIa inhibitors.

Conventional treatments for symptomatic brain neoplasms such as brain tumors, gliomas and meningiomas are surgery, radiation therapy, and chemotherapy. Most patients with clearly identified tumors undergo surgery to resect as much of the tumor as possible unless they are contraindicated for surgery. Active agent administration in conventional chemotherapy is performed systemically.

Chemotherapy is aimed at destruction of malignant cells using a variety of antineoplastic agents that directly affect cellular growth and development. The agents can slow the growth of cancer cells and keep the cancer from spreading to other parts of the body. When a cancer has been removed by surgery, chemotherapy may be used to keep the cancer from coming back (adjuvant therapy). Chemotherapy can also ease the symptoms of cancer.

The chemicals and drugs used in the treatment of cancer may be divided into several main groups. (1) Alkylating agents are capable of damaging the DNA of cancer cells, thereby interfering with the process of replication; they are cell cycle phase nonspecific. (2) Antimetabolites interfere with the cancer cell's metabolism. Some replace essential metabolites without performing their functions, while others compete with essential components by mimicking their functions and thereby inhibiting the manufacture of protein in the cell. (3) Antitumor antibiotics are isolated from microorganisms and affect the function and/or synthesis of nucleic acids; they are cell cycle phase nonspecific. (4) Alkaloids are cell cycle phase specific and exert their effect during the M phase of cell mitosis and causing metaphase arrest. (5) Hormones and antihormones create an unfavorable environment for cancer cell growth.

Chemotherapy or radiation therapy may then be a follow-up treatment to kill any remaining tumors cells. Oncology drugs approved by FDA to treat brain cancer include: Afinitor (Everolimus), Avastin (Bevacizumab), CeeNu (Lomustine), Methazolastone (Temozolomide) and Carmustine.

Methods of treatment with a bioresorbable scaffold with targeted local delivery of antineoplastic agents may provide the benefits of conventional systemic therapy. Doses of antineoplastic agents administrable by, for example, a 12 mm long scaffold range from as low as 50 μg for protease located in a coating to as high as 5 mg for protease incorporated into the scaffold backbone. However, the drug is used more efficiently since the dose is targeted to a specific region of tissue. Additionally, since the dose is targeted, a patient may suffer from no side effects or fewer side effects than systemic delivery.

Embodiments include a bioresorbable device including a bioresorbable body and an antineoplastic agent associated with the bioresorbable body. A method of treatment includes implanting the bioresorbable device in a cerebral artery supplying blood to a brain neoplasm of a patient in need of the treatment or amelioration thereof. When the device is implanted in a patient, the antineoplastic agent is released and contacts the brain tissue affected with a neoplasm and kills or slows growth of malignant cells in the tissue. The various embodiments disclosed for associating active agents with a bioresorbable scaffold and delivering active agents apply to the above-mentioned active agents for the treatment of brain neoplasms.

The treatment with the bioresorbable delivery device, i.e., local treatment, can be performed after resection of the neoplasm, as a substitute for or in addition to conventional chemotherapy or systemic administration in general. Alternatively, treatment with the bioresorbable drug delivery device can be performed as primary therapy without resection of a neoplasm. Conventional chemotherapy or systemic administration can be performed in addition to the treatment with the bioresorbable delivery device.

When a combined local and system treatment is performed, the treatments can be performed simultaneously or one can be performed prior to the other. In a combined treatment, the same active agents can be used for local and systemic treatment or different active agents may be used.

Figure 2:
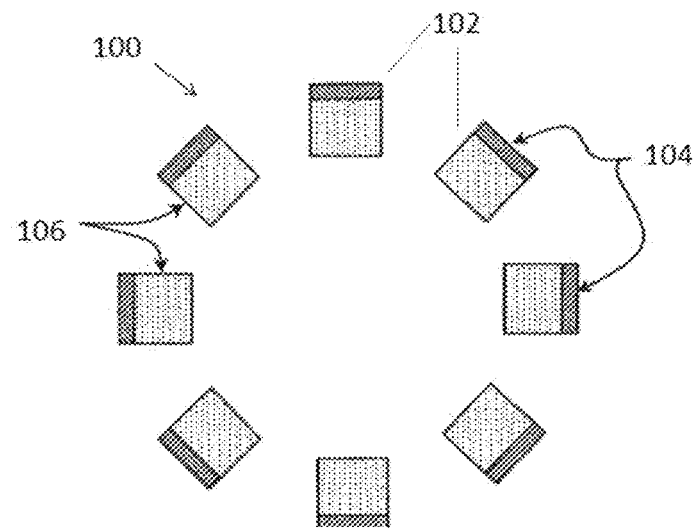
FIG. 2 depicts a cross section of scaffold composed of struts for delivering active agent into the bloodstream.

A scaffold may be designed so that drug delivery is directed into the bloodstream and not into the surrounding, abluminal tissue. FIG. 2 depicts a cross section of one such a design showing scaffold 100 composed of struts 102. Struts 102 include a luminal layer 106 and an abluminal layer 104. Layer 106 is a reservoir of resorbable polymer combined with active agent. Abluminal layer 104 may be a resorbable polymer that has a low permeability to drug. An impermeable or low permeability resorbable polymer may be a high crystallinity polymer (e.g., greater than 20%, 30%, or 40%) such as PLLA, PDLLA, or simply the same polymer as that used in the drug reservoir only with no drug in it. For many bioresorbable polymers, the drug permeability is very low and a high loading of drug is required to make the polymer permeable. The drug reservoir polymer could be PCL, PDLLA, or a PLGA. The implanted scaffold supplies drug to the bloodstream that directly feeds the tumor or affected region.

Figure 3:
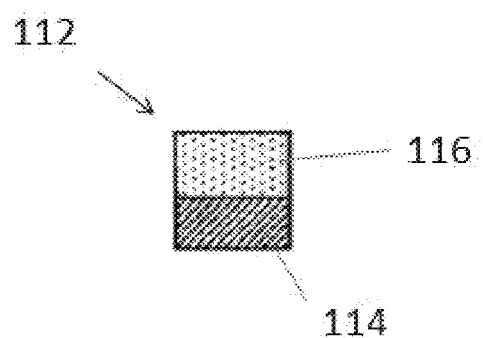
FIG. 3 depicts a cross section of a strut of a scaffold for delivering active agent into tissue of the vessel walls.

In other embodiments, the scaffold may also be implanted in an artery that lies directly within the tumor. In this case, the scaffold would be designed to release drug into the surrounding tissue rather than into the bloodstream as depicted in FIG. 3. FIG. 3 depicts a cross section of a single strut 112 of a bioresorbable scaffold designed to deliver drug into the vessel wall. Layer 116 is an abluminal layer composed of a resorbable polymer and drug. Layer 114 is a luminal layer of drug impermeable resorbable polymer.

As discussed herein, such a structure as shown in FIG. 3 might be produced by coextruding a tube of the two layers and then cutting a scaffold from the tube.

A concern regarding a vascular scaffold in the cerebral vasculature is the risk of thrombosis leading to occlusion. This would create an embolic stroke. In the case of placing a scaffold in an artery feeding a tumor, or placed upstream of a tumor, thrombotic occlusion would be a more tolerated event since it would primarily affect diseased tissue. The radial strength and recoil of the scaffold may only what is necessary to hold the scaffold in place. A balloon expandable scaffold could be used for drug delivery, but a self-expanding scaffold, for example, scaffold concepts built from braided fibers or other low radial force designs.

Radiation treatment may also be used for treatment of brain tumors. Stereotactic radiosurgery is often used where a beam of radiation exposes the tumor from multiple orientations. This reduces the radiation dose to the surrounding tissue and maximizes the dose for the tumor. Such a spatially selective radiation therapy may be delivered via a bioresorbable scaffold in the form of a radioactive source placed on the scaffold. The purpose of the scaffold becomes enabling delivery of the radioactive source to the tumor site and holding it in the vasculature. The half-life of the radioisotope may be selected so that by the time the scaffold is resorbed, the radioactivity of the source has largely decayed.

Systemic administration can be accomplished orally or parenterally including intravascularly, rectally, intranasally, intrabronchially, or transdermally.

The "glass transition temperature," Tg, is the temperature at which the amorphous domains of a polymer change from a brittle vitreous state to a solid deformable or ductile state at atmospheric pressure. In other words, the Tg corresponds to the temperature where the onset of segmental motion in the chains of the polymer occurs. When an amorphous or semi-crystalline polymer is exposed to an increasing temperature, the coefficient of expansion and the heat capacity of the polymer both increase as the temperature is raised, indicating increased molecular motion. As the temperature is increased, the heat capacity increases. The increasing heat capacity corresponds to an increase in heat dissipation through movement. Tg of a given polymer can be dependent on the heating rate and can be influenced by the thermal history of the polymer as well as its degree of crystallinity. Furthermore, the chemical structure of the polymer heavily influences the glass transition by affecting chain mobility.

The Tg can be determined as the approximate midpoint of a temperature range over which the glass transition takes place. [ASTM D883-90]. The most frequently used definition of Tg uses the energy release on heating in differential scanning calorimetry (DSC). As used herein, the Tg refers to a glass transition temperature as measured by differential scanning calorimetry (DSC) at a 10-20° C./min heating rate.

The Tg of a polymer, unless otherwise specified, can refer to a polymer that is in a dry state or wet state. The wet state refers to a polymer exposed to blood, water, saline solution, or simulated body fluid. The Tg of the polymer in the wet state can correspond to soaking the polymer until it is saturated.

"Stress" refers to force per unit area, as in the force acting through a small area within a plane. Stress can be divided into components, normal and parallel to the plane, called normal stress and shear stress, respectively. Tensile stress, for example, is a normal component of stress applied that leads to expansion (increase in length). In addition, compressive stress is a normal component of stress applied to materials resulting in their compaction (decrease in length). Stress may result in deformation of a material, which refers to a change in length. "Expansion" or "compression" may be defined as the increase or decrease in length of a sample of material when the sample is subjected to stress.

"Strain" refers to the amount of expansion or compression that occurs in a material at a given stress or load. Strain may be expressed as a fraction or percentage of the original length, i.e., the change in length divided by the original length. Strain, therefore, is positive for expansion and negative for compression.

"Strength" refers to the maximum stress along an axis which a material will withstand prior to fracture. The ultimate strength is calculated from the maximum load applied during the test divided by the original cross-sectional area.

"Modulus" may be defined as the ratio of a component of stress or force per unit area applied to a material divided by the strain along an axis of applied force that results from the applied force. The modulus typically is the initial slope of a stress—strain curve at low strain in the linear region.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method for delivering an active agent to a patient that is capable of rendering a pathogenic protein that causes a neurological disease in the central nervous system nonpathogenic, comprising:
    implanting a bioresorbable scaffold in the lenticulostriate branches of the middle cerebral artery upstream of the substantia nigra region or the basal ganglia of a patient in need of treatment or amelioration of Huntington's or Parkinson's disease, wherein the bioresorbable scaffold comprises an active agent,
    wherein the active agent is capable of rendering a pathogenic protein from the substantia nigra region or the basal ganglia that causes the disease nonpathogenic,
    wherein the active agent moves downstream from the implanted scaffold to come into contact with the pathogenic protein.

2. The method of claim 1, wherein the bioresorbable scaffold completely resorbs upon completion of active agent delivery.

3. The method of claim 1, wherein the active agent is a protease that renders the protein nonpathogenic by cleaving the protein.

4. The method of claim 1, wherein the active agent is selected from the group consisting of an exoprotease; an endoprotease; and a combination thereof.

5. The method of claim 1, wherein the protein is rendered nonpathogenic upon cleavage by the active agent of one or more glutamine-glutamine bonds in the protein.

6. A method for delivering an active agent to a patient that is capable of rendering a pathogenic protein that causes a neurological disease in the central nervous system nonpathogenic, comprising:
    implanting a bioresorbable scaffold in the lenticulostriate branches of the middle cerebral artery upstream of the substantia nigra region or the basal ganglia of a patient with no symptoms of Huntington's disease, wherein the bioresorbable scaffold comprises an active agent, and
    wherein the active agent from the implanted scaffold moves downstream and comes into contact with a pathogenic protein from the substantia nigra region or the basal ganglia that causes Huntington's disease.

7. The method of claim 6, wherein the active agent is a protease that renders the protein nonpathogenic by cleaving the protein.

8. The method of claim 6, wherein the protein is rendered nonpathogenic upon cleavage by the active agent of one or more glutamine-glutamine bonds in the protein.

* * * * *